(12) United States Patent
Dotor De Las Herrerías et al.

(10) Patent No.: US 7,666,841 B2
(45) Date of Patent: Feb. 23, 2010

(54) PEPTIDES WITH THE CAPACITY TO BIND TO TRANSFORMING GROWTH FACTOR β1 (TGF-β1)

(75) Inventors: Javier Dotor De Las Herrerías, Navarra (ES); Ana Belen Lopez Vazquez, Asturias (ES); Juan Jose Lasarte Sagastibelza, Navarra (ES); Jesus Prieto Valtuena, Navarra (ES); Francisco Borras Cuesta, Navarra (ES)

(73) Assignee: Proyecto de Biomedicina Cima, S.L., Pamplona-Navarra (ES)

( * ) Notice: Subject to any disclaimer, the term of this patent is extended or adjusted under 35 U.S.C. 154(b) by 80 days.

(21) Appl. No.: 10/569,012

(22) PCT Filed: Jul. 5, 2004

(86) PCT No.: PCT/ES2004/000320

§ 371 (c)(1),
(2), (4) Date: Aug. 11, 2006

(87) PCT Pub. No.: WO2005/019244

PCT Pub. Date: Mar. 3, 2005

(65) Prior Publication Data

US 2007/0142275 A1    Jun. 21, 2007

(30) Foreign Application Priority Data

Aug. 22, 2003 (ES) ............................... 200302020

(51) Int. Cl.
*A61K 38/08* (2006.01)
*A61K 38/10* (2006.01)
*C07K 7/06* (2006.01)
*C07K 7/08* (2006.01)

(52) U.S. Cl. ........................ 514/14; 514/15; 530/326; 530/327; 530/328

(58) Field of Classification Search ................. None
See application file for complete search history.

(56) References Cited

FOREIGN PATENT DOCUMENTS

| ES | 2146552 | 8/2000 |
|---|---|---|
| JP | 8151396 | 6/1996 |
| WO | 0024782 | 5/2000 |

OTHER PUBLICATIONS

Ishikawa, S. et al., "GD1α-replica peptides functionally mimic GD1α, an adhesion molecule of metastatic tumor cells, and suppress the tumor metastasis," FEBS Letters, 1998, vol. 441, pp. 20-24.
Dotor De Las Herrerias et al., "International Search Report," Oct. 8, 2004.

*Primary Examiner*—Marianne P Allen
(74) *Attorney, Agent, or Firm*—Tristan A. Fuierer; Moore & Van Allen, PLLC

(57) ABSTRACT

The described peptides possess the capacity to bind to Transforming Growth Factor TGF-β1 (TGF-β1), and are potential inhibitors of the biological activity of TGF-β1 through direct binding to this cytokine. These peptides can be used in the treatment of diseases or pathological alterations based on excessive or deregulated TGF-β1 expression.

10 Claims, 5 Drawing Sheets

SEQUENCE LISTING

<160> NUMBER OF SEQ ID NOS: 36

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Asp Arg Arg Ile Phe Trp Trp Ser Leu Arg Ser Ala Pro Gly Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Asp Arg Arg Ile Phe Trp Trp Ser Asn Arg Ser Ala Pro Gly Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Arg Phe Phe Thr Arg Phe Pro Trp His Tyr His Ala Ser Arg Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Arg Leu Ala His Ser His Arg His Arg Ser His Val Ala Leu Thr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Arg Arg Trp Val Arg Tyr Pro Val His Leu His Ser Pro Ile Val
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

-continued

```
Pro Pro Tyr His Arg Phe Trp Arg Gly His Arg His Ala Val Gln
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

His Arg Ile Ser His Phe Ala His Arg Tyr Leu Ala Arg Leu His
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Trp His Trp Arg His Arg Ile Pro Leu Gln Leu Ala Ala Gly Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Gly Trp His Ser Leu Leu His Ser Arg Tyr His Arg Ile Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Phe Val Trp Val Arg Phe His Arg Leu Pro Arg Gln Ile Tyr Thr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Artificial Sequence

<400> SEQUENCE: 11

Trp His Lys Tyr Phe Leu Arg Arg Pro Leu Ser Val Arg Thr Arg
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Trp His Lys Tyr Phe Leu Arg Arg Pro Leu Ser Val Gly Leu Gly
```

-continued

```
                1               5                   10                  15
```

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

```
Arg Lys Trp Phe Leu Gln His Arg Arg Met Pro Val Ser Val Leu
1               5                   10                  15
```

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

```
Ser Gly Arg Arg His Leu His Arg His His Ile Phe Ser Leu Pro
1               5                   10                  15
```

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

```
Gly Trp Ile Thr Phe His Arg Arg His His Asp Arg Val Leu Ser
1               5                   10                  15
```

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

```
Arg Leu His Gly His Arg Ser His Arg Phe Thr His Val Ala Gln
1               5                   10                  15
```

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct

<400> SEQUENCE: 17

```
Lys Arg Ile Trp Phe Ile Pro Arg Ser Ser Trp Tyr Glu Arg Ala
1               5                   10                  15
```

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

```
Met Pro Leu Ser Arg Tyr Trp Trp Leu Phe Ser His Arg Pro Arg
1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Arg His Leu Ser His Phe Lys Trp Leu Arg Ser His Gly Leu Asp
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Arg Arg Phe His Phe His Ser Arg Met Val Ala Val Asp Asn Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

His Val Arg Leu His His Tyr Leu Arg His Arg Ser Leu Pro Asn
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Val Pro Met Ala Leu Asn His Gly Val Tyr Val Met Val Ser Ser
1               5                   10                  15

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct

<400> SEQUENCE: 23
tgaattttct gtatgagg                                                      18

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Arg Ile Trp Phe Ile Pro Arg Ser Ser Trp Tyr Glu Arg Ala
1               5                   10
```

```
<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Arg Ile Trp Phe Ile Pro Arg Ser Ser Trp Tyr Glu Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Ile Trp Phe Ile Pro Arg Ser Ser Trp Tyr Glu Arg Ala
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Ile Trp Phe Ile Pro Arg Ser Ser Trp Tyr Glu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Trp Phe Ile Pro Arg Ser Ser Trp Tyr
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Trp Phe Ile Pro Arg Ser Ser Trp Tyr Glu Arg Ala
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Phe Ile Pro Arg Ser Ser Trp Tyr Glu Arg Ala
1               5                   10

<210> SEQ ID NO 31
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Ile Pro Arg Ser Ser Trp Tyr Glu Arg Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Pro Arg Ser Ser Trp Tyr Glu Arg Ala
1               5

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Lys Arg Ile Trp Phe Ile Pro Arg Ser Ser Trp Tyr Glu Arg
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Lys Arg Ile Trp Phe Ile Pro Arg Ser Ser Trp Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Lys Arg Ile Trp Phe Ile Pro Arg Ser Ser
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Lys Arg Ile Trp Phe Ile Pro Arg Ser
1               5
```

PEPTIDES WITH THE CAPACITY TO BIND TO TRANSFORMING GROWTH FACTOR β1 (TGF-β1)

CROSS-REFERENCE TO RELATED APPLICATIONS

This application is filed under the provisions of 35 U.S.C. §371 and claims the priority of International Patent Application No. PCT/ES2004/000320 on Jul. 5, 2004, which in turn claims priority of Spanish Application No. P200302020 filed on Aug. 22, 2003.

FIELD OF THE INVENTION

The invention generally refers to peptides with the capacity to bind to transforming growth factor β1 (TGF-β1), and their applications. In particular, the invention refers to peptides that inhibit the biological activity of TGF-β1 as a result of direct bonding to TGF-β1, and to their use in the treatment of diseases or pathological alterations based on the excessive or deregulated expression of TGF-β1.

BACKGROUND OF THE INVENTION

TGF-β1 is a glycoprotein belonging to a superfamily of structurally related regulatory proteins (cytokines) included within one of the three isoforms described in mammals (TGF-β1, 2 and 3). The most abundant isoform is TGF-β1, which consists of a 25 kDa homodimer composed of two subunits joined by a disulfide bond. The amino acid sequence of human TGF-β1 has been described by authors such as Derynck K et al., "Human transforming growth factor-beta complementary DNA sequence and expression in normal and transformed cells". Nature 316 (6030), 701-705 (1985).

TGF-β1 is a molecule with a highly preserved sequence in evolutive terms. Although it was originally defined by its capacity to induce adhesion independent of proliferation and morphological changes in rat fibroblasts, subsequent investigations have shown that TGF-β1 is a general inhibitor of proliferation of a broad range of cell types. The molecule is produced by a great variety of cell types and in different tissues during all phases of cell differentiation. It has a large series of biological effects, with the generation of potent and very often opposite effects in relation to development, physiology and immune response. Information on the role of TGF-β1 in liver regeneration and differentiation, and in liver fibrosis, as well as on the effects of the molecule upon the extracellular matrix, can be found in Spanish patent application ES 2146552 A1.

With the purpose of exploring the mechanism of action of TGF-β1, some ten proteins (membrane receptors and extracellular matrix proteins) have been reported to interact with this cytokine.

On the other hand, since many diseases or pathological alterations are associated with excessive or deregulated expression of TGF-β1, e.g., fibrosis associated to organ or tissue function loss, or surgical or esthetic complications, it is of interest to search for products capable of inhibiting the biological activity of TGF-β1—since such products can be potentially used in human or animal therapy to block the pathological consequences of excessive or deregulated TGF-β1 expression.

Several strategies have been used to inhibit the biological activity of TGF-β1 including the use of: (i) specific neutralizing antibodies; (ii) antisense oligonucleotides sequences of the gene encoding TGF-β1 which block its expression; or (iii) soluble receptors for TGF-β1 that act in a way similar to antibodies. The use of antibodies affords total and specific blockage of this cytokine (TGF-β1), though certain side effects are enhanced by both the presence of exogenous immunoglobulins in blood and the effects derived from the systemic blockage of TGF-β1. In addition, immunoglobulin stability over time does not allow short-time control of the blocking activity of this cytokine. Antisense oligonucleotides sequences inhibit TGF-β1 production at gene expression level—a fact that can generate important deregulation of all processes in which this cytokine participates.

Another strategy has recently been developed, based on the use of peptides that inhibit the biological activity of TGF-β1. In this sense, Spanish patent application ES 2146552 A1 describes some synthetic peptides originating from both TGF-β1 and its receptors, or from proteins capable of binding to TGF-β1, and which can be used as inhibitors of the biological activity of TGF-β1.

SUMMARY OF THE INVENTION

The invention in general addresses the problem of seeking new compounds capable to inhibit the biological activity of TGF-β1.

The solution provided by the present invention is based on the fact that the inventors have identified a series of peptides capable not only of binding to TGF-β1 but also of inhibiting the biological activity of TGF-β1 through direct binding to the latter. Some of these peptides have been identified using a technology associated to phage-displayed peptide libraries that allow the identification of peptides, with a typical size in the range of 6 to 15 amino acids, capable of binding with high affinity to TGF-β1, quantifying, subsequently, by in vitro and in vivo assays their capacity to inhibit the biological activity of TGF-β1. Other peptides have been obtained through truncation of peptides previously identified with this technology associated with phage libraries.

Peptides capable of binding to TGF-β1, and in particular those able to inhibit the biological activity of TGF-β1, by its direct bonding to TGF-β1, are potentially useful for the treatment of diseases and pathological alterations associated with excessive or deregulated expression of TGF-β1. Likewise, peptides capable of binding to TGF-β1 offer a tool for studying the biological role of TGF-β1 (an aspect that remains to be clarified in many areas of the regulation of different biological processes).

Thus, one aspect of this invention relates to peptides capable of binding to TGF-β1. In a particular and preferred embodiment, these peptides are, also, able to inhibit the biological activity of TGF-β1.

In another aspect, the invention relates to a pharmaceutical composition comprising at least one of the mentioned peptides.

In another aspect, the invention relates to the use of said peptides for the preparation of a pharmaceutical composition for the treatment of diseases and pathological alterations associated with excessive or deregulated TGF-β1 expression. Representative examples of such diseases or pathological alterations associated with excessive or deregulated TGF-β1 expression include fibrosis associated with tissue or organ function loss, as well as surgical and/or esthetic complications.

In another aspect, the invention relates to DNA sequences that encode said peptides.

In another aspect, the invention relates to a DNA construct comprising a sequence of DNA that encodes a peptide provided by this invention.

In another aspect, the invention relates to a vector comprising said DNA sequence or DNA construct.

In another aspect, the invention relates to a host cell, such as a transformed host cell, that comprises said DNA construct or vector.

In another aspect, the invention relates to a process for producing a peptide provided by this invention which comprises culturing said host cells under conditions allowing expression of said peptide, and, if desired, recovering the peptide obtained.

In another aspect, the invention relates to the use of said DNA sequences and DNA constructs in the manufacture of vectors and cells for the treatment by gene therapy techniques of diseases and pathological alterations associated with excessive or deregulated TGF-β1 expression.

DETAILED DESCRIPTION OF THE INVENTION

Figure 1:
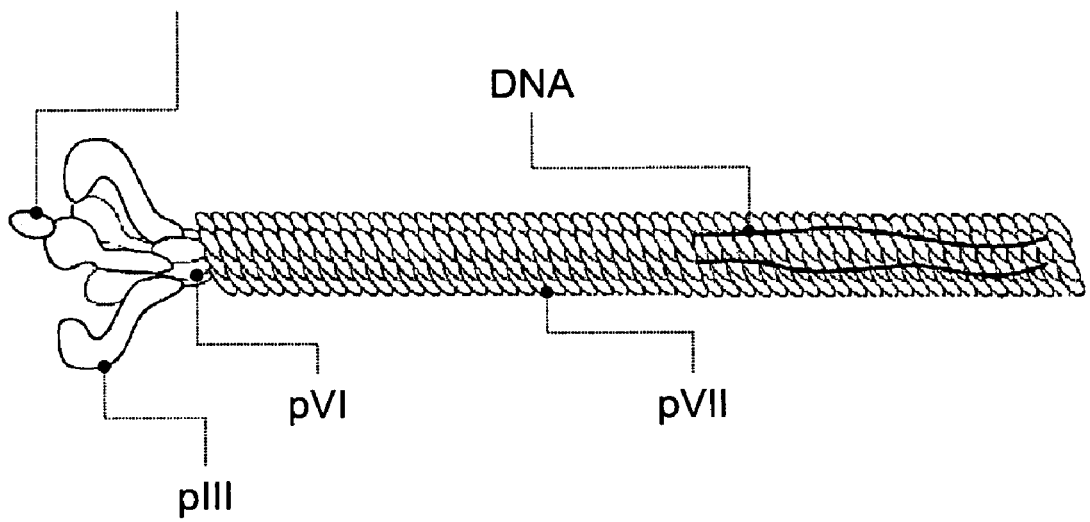
FIG. 1 schematically shows the position of a 15-amino acid (aa) peptide, genetically fused to protein pIII, on the surface of filamentous bacteriophage M13.
Figure 2:
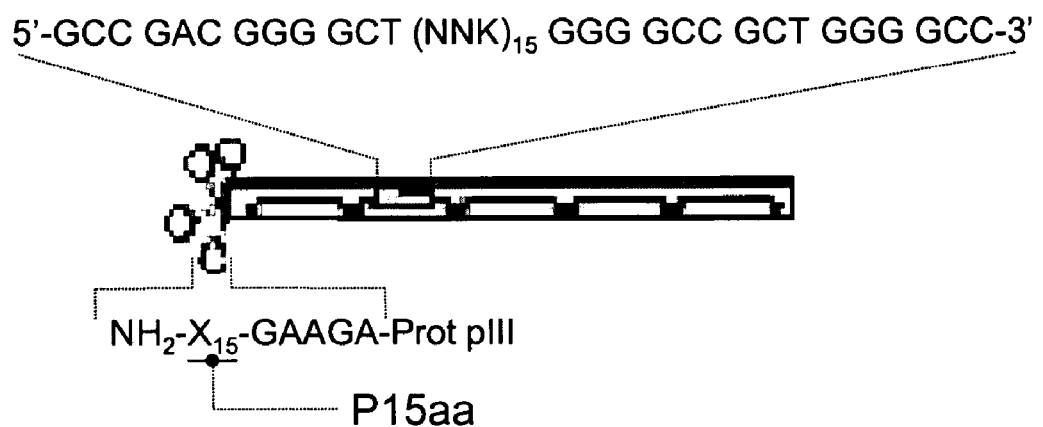
FIG. 2 schematically shows the genetic position of the insert, which encodes a 15-aa peptide, in the genome of bacteriophage M13 and the position of the peptide in the sequence of protein pIII.

In an aspect, the invention relates to a peptide, henceforth referred to as the peptide of the invention, whose amino acid sequence comprises between 3 and 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts.

The peptides of the invention are able to bind to TGF-β1. Some of these peptides are capable of inhibiting the biological activity of TGF-β1 in vitro and/or in vivo.

The capacity of the peptides of the invention to bind to TGF-β1 can be assessed by any appropriate method that allows determination of bonding between two molecules, for example, by means of an affinity assay which comprises placing TGF-β1 in contact with the testing peptide under conditions that allow bonding of the peptide to TGF-β1; and evaluating the bonding between the peptide and TGF-β1. In a particular embodiment, this affinity assay can be performed using radioactively labeled TGF-β1, e.g., human $^{125}$I-TGF-β1, as is described in ES 2146552 A1. Alternatively, the testing peptide can be the labeled component. In general, this kind of affinity assays involves placing TGF-β1 (for example, immobilized on a plate blocked with streptavidin) in contact with the testing peptide whose affinity is to be determined, and, after incubating for an appropriate incubation period of time, analysing the bonding of the peptide to TGF-β1. The peptides with low affinity for TGF-β1 are eliminated by washings, while the peptides with a high affinity remain bound to TGF-β1 and can be freed by breaking the molecular interactions between the two molecules (e.g., by lowering pH). By testing the peptide against different concentrations of TGF-β1, or viceversa, an idea can be gained of the affinity of the testing peptide for TGF-β1. The capacity of the peptides of the invention to inhibit the biological activity of TGF-β1 in vitro can be evaluated and, if desired, quantified by an Mv-1-Lu cell line growth inhibition test, a cell line derived from mink lung epithelium, the proliferation of which is inhibited by TGF-β1 (see Example 2).

The capacity of the peptides of the invention to inhibit the biological activity of TGF-β1 in vivo can be evaluated and, if desired, quantified by testing in an animal model of acute liver damage induced for example by the administration of carbon tetrachloride ($CCl_4$) (see Example 3). As it is known, acute liver damage generates a cascade of effects and physiological responses including an increase in the levels of TGF-β1, which in turn is responsible (among other effects) for the expression of type I collagen gene.

Within the scope of this invention are the pharmaceutically acceptable salts of the peptide of the invention. The term "pharmaceutically acceptable salts" includes those habitually used to form metal salts or acid addition salts. The nature of the salt is not a critical consideration, provided it is pharmaceutically acceptable. The pharmaceutically acceptable salts of the peptide of the invention can be obtained from acids or bases (organic or inorganic), based on conventional methods that are well known by the technicians in the field.

In a particular embodiment, the invention provides a peptide comprising 3, 4, 5, 6, 7, 8, 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts.

In another particular embodiment, the invention provides a peptide selected from the group formed by the peptides identified by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts.

In another particular embodiment, the invention provides a peptide selected from the group formed by the peptides identified by SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, and their pharmaceutically acceptable salts. These peptides comprise between 9 and 14 consecutive amino acid residues of the sequence of amino acids of the peptide identified by SEQ ID NO: 17, and have been obtained by truncation of said peptide (Example 4).

In another particular embodiment, the invention provides a peptide selected from the group formed by the peptides identified by SEQ ID NO: 2, SEQ ID NO: 3, SEQ ID NO: 4, SEQ ID NO: 6, SEQ ID NO: 11, SEQ ID NO: 14, SEQ ID NO: 17, SEQ ID NO: 18, SEQ ID NO: 33 and SEQ ID NO: 34, and their pharmaceutically acceptable salts. The peptides identified by SEQ ID NO: 4, SEQ ID NO: 6, SEQ ID NO: 11, SEQ ID NO: 14 and SEQ ID NO: 17, show an inhibitory capacity of the biological activity of TGF-β1, both in vitro and in vivo; the peptide identified by SEQ ID NO: 2 shows only inhibitory activity of the biological activity of TGF-β1 in vivo; while the peptides identified by SEQ ID NO: 3 and SEQ ID NO: 18 show only inhibitory activity of the biological activity of TGF-β1 in vitro. The peptides identified by SEQ ID NO: 33 and SEQ ID NO: 34 show inhibitory activity of the biological activity of TGF-β1 in vitro.

For the initial identification of peptides with the capacity of binding to TGF-β1 use has been made of the technology involving phage-displayed peptide libraries that allow determining peptides with high binding affinity for TGF-β1 and, subsequently, quantifying in vitro and in vivo their capacity to inhibit the biological activity of TGF-β1. The sequence of said peptides that bind to TGF-β1, inhibiting the biological activity of TGF-β1 in vitro or in vivo, can be deduced from the corresponding DNA sequence after various "biopanning" cycles (generally 3). The use of phage-displayed peptide libraries to identify inhibitors of certain products has been described, for example, by Chirinos-Rojas C. L. et al., in Immunology, January 1999, 96(1): 109-113; McConnell S. J., et al., in Gene, Dec. 30, 1994, 151 (1-2): 115-118; or Smith G. P., Science, Jun. 14, 1985, 228 (4705): 1315-1317.

Thus, the invention provides a method for identifying peptides capable of binding to TGF-β1, which comprises:

(i) using a phage-displayed peptide library comprising a plurality of filamentous phages, the genome of each one containing a nucleotide sequence encoding a different peptide linked to the gene encoding a phage envelope protein (thereby each phage contains a different peptide genetically fused to a protein of the phage envelope);

(ii) selecting, via an affinity assay, the phages containing the peptides that bind with increased affinity to TGF-β1; and (iii) determining the sequence of the peptides that bind to TGF-β1, based on the corresponding DNA sequences inserted in the phages selected in step (ii) and which encode said peptides that bind to TGF-β1.

In a particular embodiment, in order to obtain 15-aa peptides capable of binding with high affinity to TGF-β1, and also with an eventual inhibitory activity upon the biological activity of the mentioned cytokine, use was made of a phage-displayed peptide library comprising a plurality of filamentous bacteriophages (M13), each one containing a different 15-aa peptide genetically fused to a protein of the phage envelope, in this case bond to the N-terminal end of the envelope protein pIII. In this way the phage presents a surface with a 15-aa peptide in each one of the 5 surface protein molecules, while the DNA encoding the mentioned peptide sequence is contained within the phage. In the phage libraries the sequence encoding the peptide originates from a sequence degenerated in each one of the 15 positions with the 20 natural amino acids, thus allowing the presentation of $1.1 \times 10^{12}$ possible sequences of 15 amino acids in different phages. The physical ratio, 1:1, between the peptide sequence and the DNA encoding it within the bacteriophage allows the selection (from among a broad range of variants) of those sequences that specifically bind to TGF-β1. This process is carried out via an affinity assay.

In a particular embodiment, the mentioned affinity assay consists in an in vitro selection protocol known as "biopanning". In brief, this technique involves the incubation of a set of phages representative in practical terms of all the variants of 15-aa peptides (in this case) in a plate blocked with streptavidin and to which biotinylated TGF-β1 is added. The biotinylated TGF-β1 is thus anchored to the plate through the biotin-streptavidin bond thus being correctly displayed for its interaction of TGF-β1 with the peptides carried by the phages. Following incubation, the unbound phages are eliminated by washings, and the specifically bound phages are then specifically eluted by lowering the pH, a procedure that breaks the molecular interactions between TGF-β1 and the peptides presented by the phages. The eluted phages are then amplified via infection in a bacterial strain. The procedure is repeated 3 cycles, so that an enrichment in the content of phages which specifically bind, and with high affinity, to TGF-β1 is achieved. The concentration of biotinylated TGF-β1 used to block the plates is gradually reduced in each cycle, e.g., from 2.5 to 0.01, and finally to 0.001 μg/ml. Thus, at the end of the process, phages which have been selected by their affinity to TGF-β1 are sequenced using primers. This allows obtaining the sequence of the peptides presented by the phages.

Example 1 shows the selection of peptides that bind to TGF-β1 via phage libraries, "biopanning" selection, and sequencing of the peptides that bind with high affinity to TGF-β1.

The invention also provides a method for the identification of peptides capable of binding to TGF-β1 which comprises truncation of the peptides that are able to bind to TGF-β1, followed by testing the capacity of these truncated peptides to bind to TGF-β1. The truncated peptides can be obtained by any conventional method, such as for example chemical synthesis (in view of their size) of the peptide versions truncated at the N-terminal or C-terminal ends. The capacity of these truncated peptides to bind to TGF-β1 can be determined using any appropriate method to characterize binding between two molecules, e.g., an affinity assay, which involves placing TGF-β1 in contact with the testing peptide under conditions allowing binding of the mentioned peptide to TGF-β1 and evaluating the binding of the peptide to TGF-β1, as it has been mentioned above. Likewise, the capacity of these truncated peptides to inhibit the biological activity of TGF-β1 in vitro and/or in vivo can be tested by any of the methods mentioned in this description.

Due to the role played by TGF-β1 in many biological processes, a consequence of the TGF-β1 inhibitory activity of the peptides of the invention has to do with the potential development of a family of drugs for the treatment of diseases and pathological alterations associated with excessive or deregulated TGF-β1 expression, since such peptides can block the damage-induced by excessive or deregulated expression of this cytokine.

The peptides of the invention therefore can be used in the treatment of diseases or pathological alterations associated to excessive or deregulated TGF-β1 expression, such as: (i) fibrosis associated to organ or tissue function loss, e.g., pulmonary fibrosis, liver fibrosis (cirrhosis), renal fibrosis, corneal fibrosis, etc.; and (ii) surgical and/or esthetic complications, e.g., fibrosis associated to skin and peritoneal surgery, fibrosis associated with burns, osteoarticular fibrosis, keloids, etc.

Thus, in another aspect, the invention relates to a pharmaceutical composition comprising a therapeutically effective amount of a peptide of the invention together with at least one pharmaceutically acceptable excipient. The pharmaceutical composition provided by this invention can contain one or more peptides of the invention, optionally in combination with one or more alternative TGF-β1 inhibiting compounds. This pharmaceutical composition is useful for administration and/or application to the human or animal body (preferably in the former).

The use of peptides such as those of the present invention, instead of antibodies or antisense oligonucleotides sequences, offers many advantages, since these are small molecules with higher diffusion potential and a shorter half-life. The peptides can exhibit high affinity for TGF-β1, though they degrade faster than antibodies, nevertheless, the side effects may be controlled by dosage. Vehiculization of the peptides to target organs and tissues is also easier compared with other types of compounds.

The peptides of the invention can be administered to treat diseases and pathological alterations associated with excessive or deregulated TGF-β1 expression via any means that place the peptide of the invention in contact with its action site or target within the human or animal body. The amount of peptide, derivative or pharmaceutically acceptable salt that can be present in the pharmaceutical composition provided by this invention can vary over a considerable range.

The dosage indicated to treat a disease or pathological alteration associated with excessive or deregulated TGF-β1 expression using the peptides and/or pharmaceutical compositions of the invention will depend on numerous factors—including patient age, condition, the severity of the background disorder or pathological alteration, and the route and frequency of administration of the invention peptide involved.

The pharmaceutical compositions containing the peptides of the invention can be formulated in any form of administration, e.g., solid or liquid, and can be administered via any appropriate route, e.g., oral, parenteral, rectal or topical. To this effect, acceptable pharmaceutical excipients needed for the formulation of the desired administration form must be included, such as for example ointments (lipogels, hydrogels, etc.), eyedrops, nebulization aerosols, injectable solutions, osmotic pump systems, etc. A review of the different drug dosage forms and of the excipients required to the effect can be found, for example, in the publication "Tratado de Farmacia Galénica", C. Faulí i Trillo, 1993, Luzán 5, S.A. Ediciones, Madrid.

The use of peptides of the invention in the manufacture of the mentioned pharmaceutical composition constitutes an additional aspect of this invention. Thus, in another aspect, the invention relates to the use of a peptide of the invention in the manufacture of a pharmaceutical composition for the treatment of diseases or pathological alterations associated with excessive or deregulated TGF-β1 expression, such as fibrosis associated with organ or tissue function loss, e.g., pulmonary fibrosis, liver fibrosis (cirrhosis), renal fibrosis, corneal fibrosis, etc.; and surgical and/or esthetic complications, e.g., fibrosis associated to skin and peritoneal surgery, fibrosis associated with burns, osteoarticular fibrosis, keloids, etc.

The peptides of the invention can be obtained by conventional methods, such as for example by solid phase chemical synthesis, purified with high performance liquid chromatography (HPLC), and, if desired, analyzed by conventional techniques such as for example sequencing and mass spectrometry, amino acid analysis, nuclear magnetic resonance techniques, etc.

Alternatively, the peptides of the invention can be obtained by recombinant DNA technology. Thus, in another aspect, the invention yields a DNA sequence encoding a peptide of the invention. Said DNA sequence can easily be deduced from the amino acid sequence of the peptide.

Said DNA sequence can be contained within a DNA construct. Thus, the invention yields a DNA construct comprising a sequence of DNA that encodes a peptide of the invention. This DNA construct can operatively incorporate a regulatory sequence for the expression of the DNA sequence encoding the peptide of the invention. Control sequences are sequences that control and regulate the transcription and, where applicable, the translation of the peptide of the invention; they include promoter and terminator sequences, etc., which are functional in transformed host cells, that comprise the mentioned DNA sequence or DNA construct. In a particular embodiment, said control expression sequence is functional in bacteria. Advantageously, this DNA construct also comprises a marker or gene that encodes a motif or phenotype which allows selection of the transformed host cell by means of the DNA construct. The DNA construct provided by this invention can be obtained by means of methods which are well known in the state of the art [Sambrook et al., "Molecular cloning, a Laboratory Manual", $2^{nd}$ ed., Cold Spring Harbor Laboratory Press, N.Y., 1989 Vol. 1-3].

The DNA sequence or DNA construct provided by this invention can be inserted in an appropriate vector. Thus, in another aspect, the invention relates to a vector, such as an expression vector, that comprises the mentioned DNA sequence or DNA construct. The choice of vector will depend on the host cell into which it is to be inserted subsequently. As an example, the vector into which the DNA sequence is inserted can be a plasmid or vector which, upon insertion into the cell, may or may not integrate to the cell genome. The vector can be obtained by conventional methods known by the skilled person [Sambrok et al., 1989, cited supra].

In another aspect, the invention relates to a host cell, such as a transformed host cell, that comprises a DNA sequence or DNA construct provided by this invention.

In another aspect, the invention relates to a process for producing a peptide of the invention which comprises growing a host cell with the DNA sequence or DNA construct provided by the invention, under conditions that allow the production of the mentioned peptide of the invention, and, if desired, recovering the peptide of the invention. The conditions for optimizing culture of the host cell will depend on the type of host cell employed. If desired, the process for producing the peptide of the invention includes isolation and purification of the peptide.

In another aspect, the invention relates to the use of these DNA sequences and DNA constructs in the manufacture of vectors and cells for the treatment by gene therapy of diseases and pathological alterations associated with excessive or deregulated TGF-β1 expression. In accordance with this aspect of the invention, these DNA sequences or DNA constructs are placed in contact with a genetic transfer vector (e.g., a viral or non-viral vector). Appropriate viral vectors for carrying out this aspect of the invention include but are not limited to the following vectors: adenoviral, adenoassociated, retroviral, lentiviral, alphaviral, herpesviral, coronavirus derived vectors, etc. Appropriate non-viral vectors for carrying out this aspect of the invention include but are not limited to naked DNA, liposomes, polyamines, dendrimers, cationic glycopolymers, liposome-polycation complexes, proteins, receptor-mediated genetic transfer systems, etc.

The following examples illustrate the invention and should not be taken to reflect limitations to the latter.

EXAMPLE 1

Selection of Peptides that Bind to TGF-β1 Using a Phage-Displayed Peptide Library In order to obtain sequences of 15 amino acids capable of high affinity binding to TGF-β1, and offering a possible inhibitory activity upon the biological activity of this cytokine, use was made of an in vitro selection technique based on technology developed from phage-displayed peptide libraries. These libraries comprise a plurality of filamentous bacteriophages (M13), each one containing a peptide genetically fused to a protein of the virus envelope—in this case bound to the N-terminal end of envelope protein pIII (FIG. 1). In this way the phage displays a 15-aa peptide at the surface of each one of the 5 copies of the surface protein pIII, whereas the DNA sequence encoding the peptide is contained within the phage. In the phage libraries, the sequence encoding the peptide originates from a sequence degenerated in each one of the 15 positions with the 20 natural amino acids, thus allowing the presentation of $1.1 \times 10^{12}$ possible sequences of 15 amino acids in different phages. The physical ratio, 1:1, between the peptide sequence and the DNA encoding it within the bacteriophage allows the selection (from a broad range of variants) of those sequences that specifically bind to TGF-β1. This process is carried out via an in vitro selection protocol known as "biopanning".

The phage-displayed library used for this example originates from a second amplification of the primary library described by T. Nishi, H. Tsuri and H. Saya [Exp. Med. (Japan) 11, 1759 (1993)], and supplied by the laboratory of George P. Smith. Additional information on this technology can be found at the following website: http://www.biosci.missouri.edu/smithgp/PhageDisplayWebsite/PhageDisplayWebsiteIndex.html Selection Technique ("Biopanning")

Figure 3:
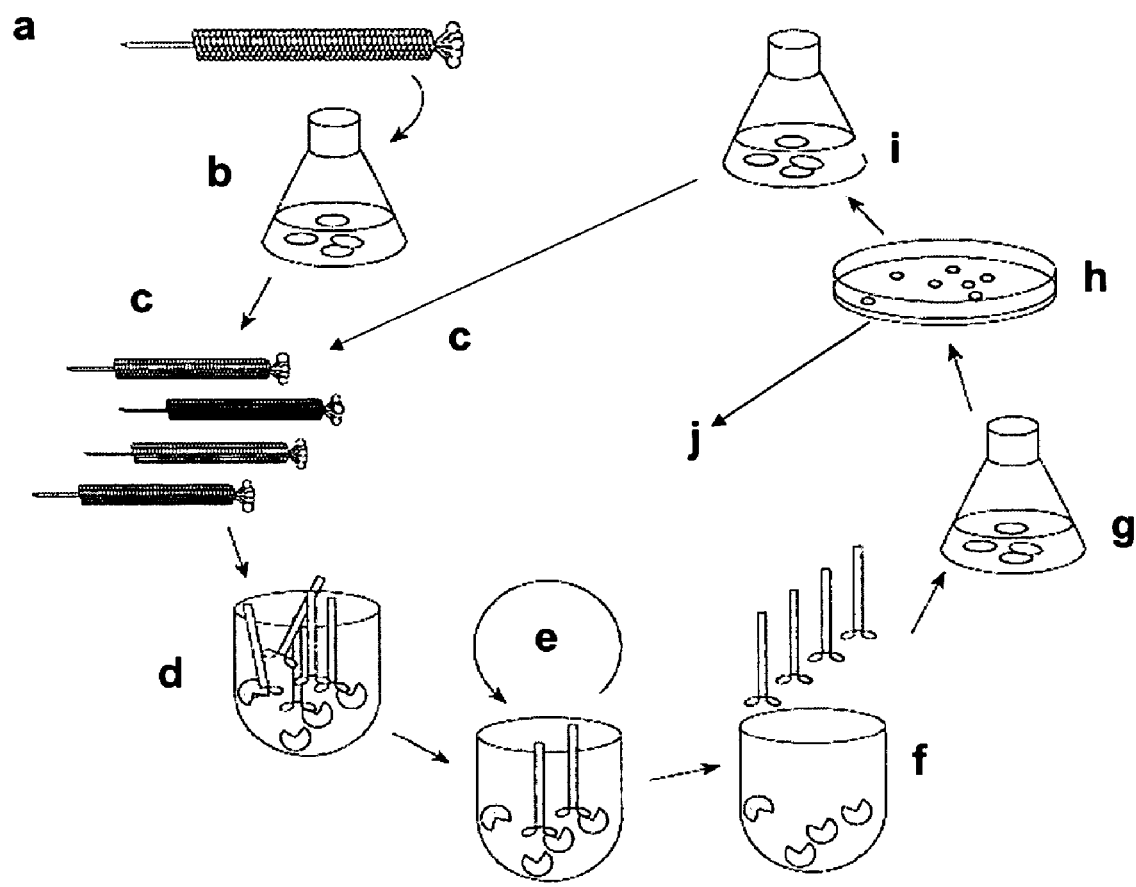
FIG. 3 schematically shows the selection of peptides based on the "biopanning" technique. The biotinylated TGF-β1 is immobilized on plates containing streptavidin (through biotin-streptavidin bonding). Phages from the library are selected on the basis of the interaction between TGF-β1 and the peptides presented by the phages. The phages with low affinity for TGF-β1 are eliminated by washings. The phages retained in the plate are eluted by lowering the pH. After three cycles of enrichment of phages with high affinity for TGF-β1, the phages are isolated and sequenced (see Example 1) [Legends to FIG. 3: "a": Library of phages presenting 15-aa peptides; "b": Infection in E. coli (K91Kan)(amplification); "c": Purification of the phages; "d": Incubation of the phages with decreasing concentrations of TGF-β1; "e": Washings; "f": Elution of the bound phages (↓pH); "g": Infection in strain of E. coli; "h": Selection of infected colonies (tetracycline); "i": Amplification of the selected phages; and "j": Sequencing of DNA (corresponding to the peptide) after three "biopanning" cycles].

This technique involves incubating a set of phages representative (to practical effects) of all the 15-aa variants, in a plate blocked with streptavidin (10 μg/ml in 0.1 M $NaHCO_3$, during 2 h at room temperature) to which biotinylated TGF-β1 is added. The biotinylated TGF-β1 is anchored to the plate through the biotin-streptavidin interaction, thereby it remains correctly displayed for its interaction with the peptides carried by the phages. TGF-β1 contacts the peptides carried by the phages at a concentration of $3 \times 10^4$ virus/ml. After about 12 hours incubation, unbound phages are eliminated by 5 washings with PBS/Tween (phosphate buffered saline/polyoxyalkylene derivatives of sorbitan fatty acid esters). Bound phages are then eluted by lowering the pH (elution buffer) which breaks the interactions between TGF-β1 and the peptides displayed by the phages. The eluted phages are then amplified by infection in a bacterial strain (*E. coli*). The process is repeated three cycles so that an enrichment in the content of phages which specifically bind, and with high affinity, to TGF-β1 is achieved (FIG. 3). The concentration of biotinylated TGF-β1 used to block the plates is gradually reduced in each cycle, e.g., from 2.5 to 0.01 μg/ml, and finally to 0.001 μg/ml. Thus, the phages selected in each cycle show more and more affinity for TGF-β1. At the end of the process, phages which have been selected for their affinity for TGF-β1, are sequenced by using primers, after isolation by tetracycline resistance of the genetically modified phages after infecting *E. coli* cells. This allows obtaining the peptides sequences displayed in the phages of a number of clones obtained from isolated colonies. The number of times which a sequence is repeated, corresponding to a 15 amino acids peptide carried by each clone, from the total of sequenced colonies is an indication of the degree of relative affinity of said 15 amino acids sequence for TGF-β1.

Sequence of Peptides

The selection of clones, obtained from the "biopanning", was carried out by selection of the bacterial colonies infected with the phages in the presence of a bacterial antibiotic; the bacteria resistance is acquired by a tetracycline resistance gene encoded by the phage genome. Thus, only those colonies infected with bacteriophages are able to grow. This means that each colony contains the genome of only one phage coding for only one peptide presented in its surface.

A total number of 108 colonies of phage-infected bacteria were obtained from the last selection cycle of "biopanning". The sequence of the regions coding for the peptides present in the pIII protein was carried out using primers identified with SEQ ID NO: 23. This afforded different peptide sequences as shown in Table 1. This table also reflects the number of colonies (clones) carrying said sequences.

TABLE 1

Amino acid sequences from phages that bind to TGF-β1

| SEQ ID NO: | No. colonies |
|---|---|
| 1 | 6 |
| 2 | 1 |
| 3 | 41 |
| 4 | 18 |
| 5 | 1 |
| 6 | 12 |
| 7 | 2 |
| 8 | 2 |
| 9 | 1 |
| 10 | 1 |
| 11 | 4 |
| 12 | 1 |
| 13 | 6 |
| 14 | 2 |
| 15 | 1 |
| 16 | 1 |
| 17 | 3 |
| 18 | 1 |
| 19 | 1 |
| 20 | 1 |
| 21 | 1 |
| 22 | 1 |

The number of clones (colonies) of each sequence gives an approximate indication of the degree of affinity of the peptide for TGF-β1, that is, the more colonies the more binding affinity. However, the degree of affinity does not correlate to the capacity of the peptide to block the biological activity of TGF-β1. Indeed, the most active peptide, identified by SEQ ID NO: 17 (see Tables 2 and 3), is represented by 3 clones, while the peptide identified by SEQ ID NO: 3, which is represented by 41 clones, is much less active in the acute liver damage assay (Table 3). While not being adhered to any concrete theory, this observation might be explained by postulating that the most active peptide probably blocks the binding of TGF-β1 to its receptor.

Comparison of the Peptide Sequences

Figure 4:
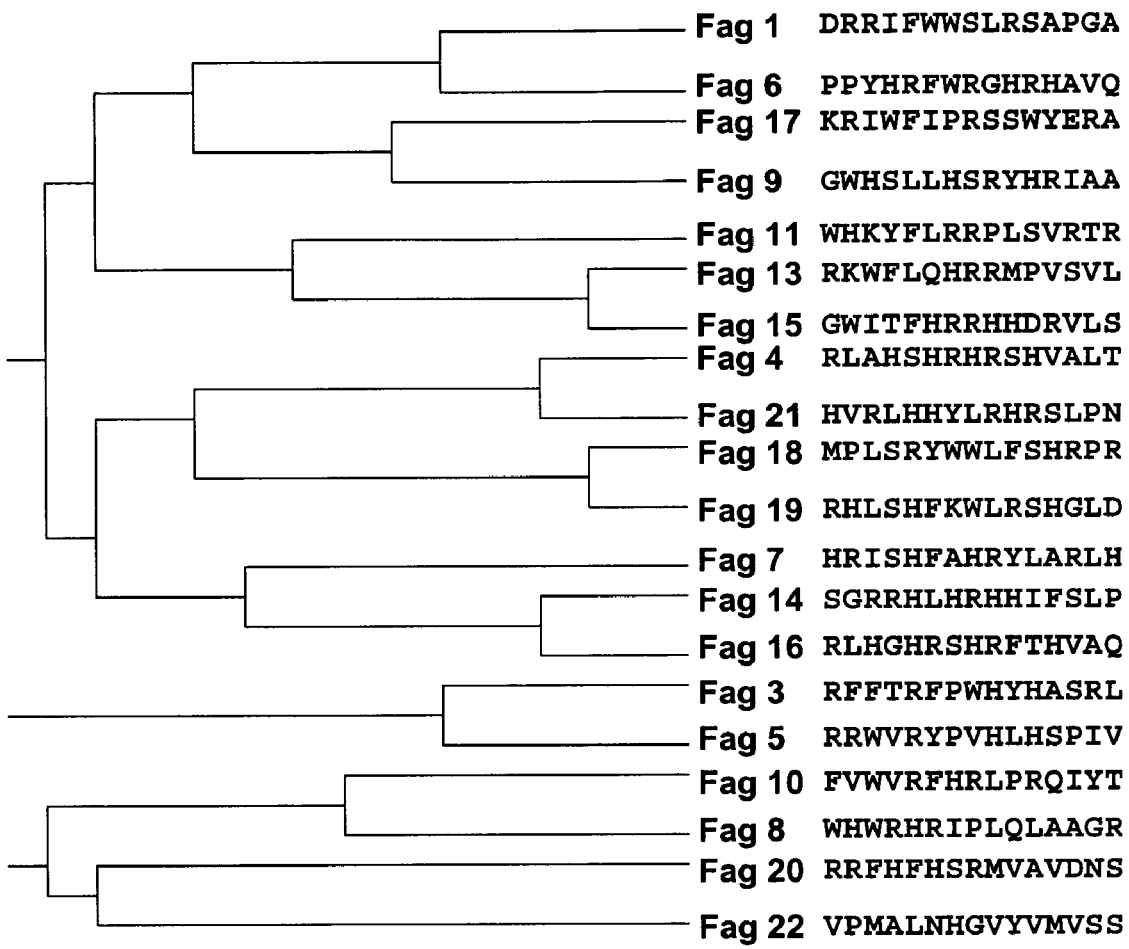
FIG. 4 provides a representation of a sequence analogy tree among the 15-aa peptides identified by means of a phage-displayed peptide library.

The sequences obtained were analyzed using the CLUSTAL W program (1.81). This program generates multiple sequences grouping based on the amino acid sequence analogies. Peptides are consequently grouped in different structural families based on sequence analogies of the peptides (FIG. 4). Based on these analogies, lesser TGF-β1 bonding motifs or groups of peptides that bind to different TGF-β1 regions can be suggested.

EXAMPLE 2

Figure 5:
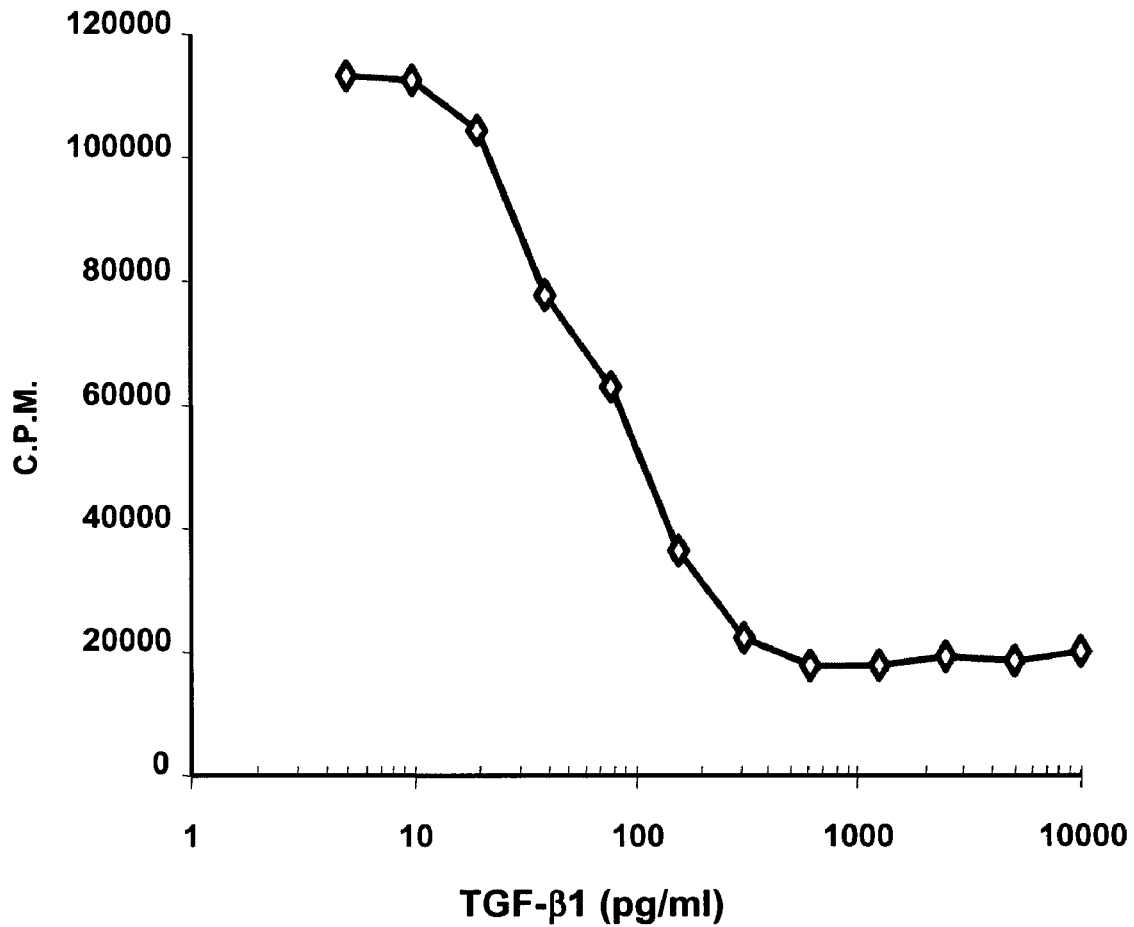
FIG. 5 provides a diagrammatic representation of the effect of TGF-β1 concentration on growth of the Mv-1-Lu cell line, expressed as the uptake of tritiated thymidine in counts per minute (c.p.m.).

Inhibition of in Vitro TGF-β1 Biological Activity by Using Peptides in Mv-1-Lu Cell Proliferation Assays The cell line Mv-1-Lu (CCL-64, American Type Cell Culture, Va., USA) derives from mink pulmonary epithelium, grows as a monolayer, and responds to the presence of TGF-β1 by decreasing its proliferation (FIG. 5). Thus, the peptide-mediated inhibition of this cytokine is able to restore cell growth and reflects the capacity of the different peptides to inhibit the biological activity of TGF-β1 in vitro. The peptides tested were obtained by peptide synthesis, in accordance to conventional procedures (Merrifield R B. J Am Chem Soc 1963; 85:2149-2154; Atherton E et al. J Chem Soc Perkin Trans 1981; 1:538-546).

The Mv-1-Lu cells are cultured to confluence in complete medium [RPMI-1640 supplemented with L-glutamine, sodium pyruvate, antibiotics and 10% fetal bovine serum (FBS)] at 37° C. and in 5% $CO_2$ in 162 $cm^2$ bottles (Costar Corporation, Calif., USA). Following trypsinization, the cells are cultured in 200 μl of complete medium in 96-well plates at an initial density of 5,000 cells/well at 37° C. and in 5% $CO_2$ during 6 hours to ensure adhesion. Then, different concentrations of the peptides to be tested are added, starting from 200 μg/ml, and following 200 μg/ml of TGF-β1 (Roche) are added. After 12 hours of incubation 1 μCi of methyl-$^3$H-thymidine (Amersham Life Science, Buckinghamshire, United Kingdom) is added per well in 25 μl of clean medium (RPMI-1640). The plate is incubated for 12 more hours under the same conditions. Finally, the cells are harvested (Filtermate 196 Harvester, Packard), transferring the tritiated thymidine, incorporated in the course of DNA synthesis, to plates (UniFilter-96 GF/C®, Perkin Elmer). Following the addition of scintillation fluid, the radioactivity was quantified using a scintillation counter (Top Count, Microplate Scintillation Counter, Packard). As positive and negative control, use was made of the incorporation of tritiated thymidine in the absence and presence of TGF-β1, respectively. The inhibition of TGF-β1 activity in this test was calculated based on the following formula:

$$\% \text{ Inhibition} = \frac{100 \times (cpm \text{ with peptide} - cpm \text{ negative control})}{(cpm \text{ positive control} - cpm \text{ negative control})}$$

The negative control represents the incorporation of tritiated thymidine in the presence of TGF-β1 but in the absence of peptide, whereas the positive control refers to the incorporation of tritiated thymidine in the absence of TGF-β1 and peptide. Thus, according to the capacity of the peptides to revert the cytokine repressor effect on Mv-1-Lu cell line proliferation, percentage of TGF-β1 biological activity inhibition by the peptides can be measured (Table 2).

TABLE 2

Effect of the peptides obtained by selection by "biopanning" on the inhibition of in vitro TGF-β1 biological activity, as calculated from a Mv-1-Lu cell line growth reestablishment assay

| SEQ ID NO: | % Inhibition |
|---|---|
| 1 | 3.33 ± 4.3 |
| 2 | −0.96 ± 0.83 |
| 3 | 25.39 ± 1.7 |
| 4 | 5.53 ± 7.2 |
| 5 | 15.78 ± 7.7 |
| 6 | 12.85 ± 4.5 |
| 7 | −24.96 ± 0.75 |
| 8 | 15.67 ± 8.5 |
| 9 | 4.98 ± 9.5 |
| 10 | −4.58 ± 0.9 |
| 11 | 27.36 ± 0.9 |
| 12 | 10.70 ± 0.9 |
| 13 | 17.97 ± 4.3 |
| 14 | 3.62 ± 5.6 |
| 15 | 13.45 ± 9.5 |
| 16 | 9.47 ± 4.2 |
| 17 | 38.92 ± 2.3 |
| 18 | 21.29 ± 2.8 |
| 19 | 9.71 ± 3.2 |
| 20 | 6.16 ± 9.5 |
| 21 | 13.40 ± 3.2 |
| 22 | 4.13 ± 1.4 |
| P144 | 7.26 ± 3.53 |

The peptides identified as SEQ ID NO: 3, 11, 17 and 18 inhibit the biological activity of TGF-β1 in vitro with a percentage of inhibition higher than 20%.

Additionally, in order to assess the capacity of the peptides to revert the suppressor effect of TGF-β1 on Mv-1-Lu cell line proliferation as previously described, the activity of the peptide identified as P144 in the Spanish patent application ES 2146552 A1 was compared with the activity of the peptide identified as SEQ ID NO: 17. The peptide identified as SEQ ID NO: 17 exhibited an improved capacity.

EXAMPLE 3

Figure 6:
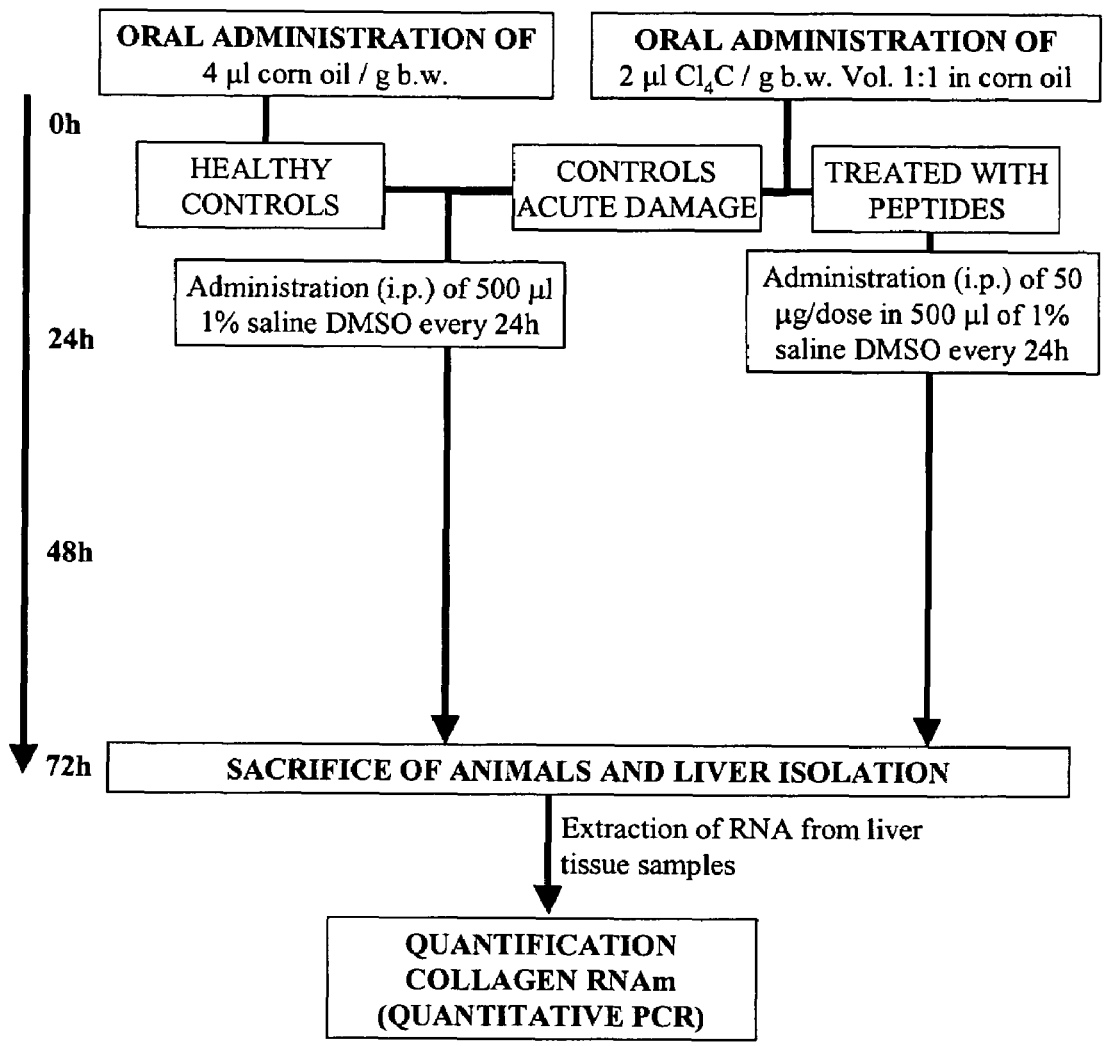
FIG. 6 provides a diagrammatic representation of the acute liver damage induction protocol (see Example 3).

In Vivo Inhibition of TGF-β1 Biological Activity by Peptides Using a Model of Acute Liver Damage Induced by $CCl_4$ Acute liver damage generates a cascade of effects and physiological responses, including elevations in the concentrations of TGF-β1. This elevation is responsible for the expression of the type I collagen gene, among others. In this model of acute liver damage, female Balb/C mice weighing 25 to 30 g, were orally administered a dose of 2 μl of $CCl_4$ (per gram of body weight) dissolved in an equivalent volume of corn oil (volumetric ratio of 1:1). The control group received an equivalent volume of corn oil only, and the treated groups received (following the single oral administration of $CCl_4$ in corn oil) 50 μg of peptide in 500 μl of 1% physiological saline solution in DMSO (dimethyl sulfoxide) every 24 h. After 72 hours all animals were sacrificed, and the liver samples were processed. To evaluate mRNA expression, liver tissue was frozen in liquid nitrogen and stored at −80° C. until further use. Other liver tissue samples were stored in OCT® or Tissue-Tek® (Sakura Finetek B.V.) and processed in the same way as the samples used for mRNA studies. Other liver samples were fixed in 10% buffered formalin solution, embedded in paraffin and processed for their histological evaluation. The amount of mRNA encoding type I collagen was quantified in all groups using a quantitative polymerase chain reaction (PCR) technique. FIG. 6 shows a flow chart of the induction, obtaining of the samples and results quantification in the acute liver damage assay. The capacity of the testing peptides to block the acute damage, as assessed by measuring the levels of induced type I collagen mRNA was quantified by real time PCR. Table 3 shows the degree of inhibition of the expression of collagen type I mRNA by phage-derived peptides. The peptides tested were obtained by conventional solid peptide synthesis procedures (Merrifield R B. J Am Chem Soc 1963; 85:2149-2154; Atherton E et al. J Chem Soc Perkin Trans 1981; 1:538-546).

TABLE 3

Effect of the peptides obtained by selection by "biopanning" on the inhibition of in vivo TGF-β1 biological activity, as calculated on the basis of the inhibition of type I collagen mRNA induction in a model of acute liver damage

| SEQ ID NO: | % Inhibition |
|---|---|
| 1 | 0.69 |
| 2 | 36.6 ± 30.7 |
| 3 | 2.09 |
| 4 | 51.30 ± 15.3 |
| 5 | Neg |
| 6 | 74.94 ± 25.3 |
| 7 | Neg |
| 8 | Neg |
| 9 | 26.59 |
| 10 | Neg |
| 11 | 39.34 ± 21.9 |
| 12 | Neg |
| 13 | 32.70 |
| 14 | 49.84 ± 24 |
| 15 | 14.26 |
| 16 | Neg |
| 17 | 93.09 ± 9.6 |
| 18 | Neg |
| 19 | 12.12 |
| 20 | 1.41 |
| 21 | Neg |
| 22 | Neg |
| P144 | −3.51 ± 36 |

(Neg: negative)

The peptides identified as SEQ ID NO: 2, 4, 6, 11, 14 and 17 inhibit the biological activity of TGF-β1 in vivo, with a percentage of inhibition greater than 35%.

Additionally, in order to assess the capacity of the peptides to inhibit type I collagen mRNA induction in a model of acute liver damage in mice as previously described, the activity of the peptide identified as P144 in the Spanish patent application ES 2146552 A1 was compared with the activity of the peptide identified as SEQ ID NO: 17. In this comparative assay, it was observed that the peptide identified as SEQ ID NO: 17 inhibits the expression of type I collagen mRNA to a much greater extent than the peptide identified as P144 in the Spanish patent application ES 2146552 A1, which does not show any activity in this assay. The results obtained by the comparative tests (Examples 2 and 3) show that a peptide representative of the peptides of this invention (the peptide identified as SEQ ID NO: 17) is more active than a peptide representative of Spanish patent application ES 2146552 A1 (the peptide identified as P144) in the proliferation tests with Mv-1-Lu cells and in a model of acute liver damage.

EXAMPLE 4

In Vitro Inhibition of TGF-β1 Biological Activity by Truncated Peptides from the Peptide of SEQ ID NO: 17 in a Proliferation Assay with Mv-1-Lu Cells This example shows the inhibitory activity of some peptides whose amino acid sequences comprise between 3 and 15 consecutive amino acid residues of one of the amino acid sequences of the invention.

Comparisons have been made of the activity of truncated peptides (derived from peptide sequence SEQ ID NO: 17) versus the complete sequence, in terms of the capacity to revert the suppressor effect of TGF-β1. upon proliferation of the Mv-1-Lu cell line. To this effect, and to determine the minimum sequence of peptide SEQ ID NO: 17 capable of inhibiting the biological activity of TGF-β1 in vitro, truncated versions of this peptide were synthesized, with truncation at the N-terminal end, C-terminal end or in both ends of the molecule. The peptides tested were obtained by peptide synthesis following conventional procedures (Merrifield R B. J Am Chem Soc 1963; 85:2149-2154; Atherton E et al. J Chem Soc Perkin Trans 1981; 1:538-546). Following the same methodology described in Example 2, the activity of truncated peptides versus the complete sequence of the peptide SEQ ID NO: 17 was quantified, in terms of a proliferation assay of the Mv-1-Lu cell line.

TABLE 4

Effect of the truncated peptides obtained from the peptide SEQ ID NO: 17 on the inhibition of in vitro TGF-B1 biological activity, as calculated from a Mv-1-Lu cell line growth reestablishment assay

| SEQ ID NO: | Sequence of peptide | % Inhibition |
|---|---|---|
| 17 | KRIWFIPRSSWYERA | 28.5 ± 3.9 |
| 24 (T1) | RIWFIPRSSWYERA | 9.4 ± 0.4 |
| 25 (T2) | RIWFIPRSSWYER | 6.2 ± 1.5 |
| 26 (T3) | IWFIPRSSWYERA | 4.5 ± 1.8 |
| 27 (T4) | IWFIPRSSWYE | 1.4 ± 2.5 |
| 28 (T5) | WFIPRSSWY | 3.1 ± 0.9 |
| 29 (T6) | WFIPRSSWYERA | 2.7 ± 1.8 |
| 30 (T7) | FIPRSSWYERA | −0.3 ± 3.0 |
| 31 (T8) | IPRSSWYERA | 3.4 ± 1.4 |
| 32 (T9) | PRSSWYERA | 3.8 ± 1.6 |
| 33 (T10) | KRIWFIPRSSWYER | 31.4 ± 7.0 |
| 34 (T11) | KRIWFIPRSSWY | 34.4 ± 7.9 |
| 35 (T12) | KRIWFIPRSS | 6.0 ± 0.4 |
| 36 (T13) | KRIWFIPRS | 6.2 ± 2.5 |

As shown in Table 4, in this comparative assay, the removal of lysine (K) from the N-terminal end implies a loss of activity of peptide SEQ ID NO: 17 from 28.5% to 9.4%. In contrast, the removal of up to three amino acids from the C-terminal end does not affect the activity of the peptide. Also, removal of the aromatic amino acids tyrosine (Y) and tryptophan (W), abrogates the activity of the peptide. This allows reducing the original peptide SEQ ID NO: 17 to a 12 amino acid sequence (KRIWFIPRSSWY) [SEQ ID NO: 34] not affecting its TGF-β1 in vitro inhibitory activity.

The invention claimed is:

1. A peptide comprising 9, 10, 11, 12, 13, or 14 consecutive amino acids of SEQ ID NO: 17 and their pharmaceutically acceptable salts, wherein the peptide is characterized by a capacity to bind to transforming growth factor β1 (TGF-β1).

2. A peptide comprising an amino acid sequence selected from SEQ ID NO: 17, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36, and their pharmaceutically acceptable salts, wherein the peptide is characterized by a capacity to bind to transforming growth factor β1 (TGF-β1).

3. The peptide according to claim 1 comprising SEQ ID NO: 17.

4. The peptide according to claim 1 comprising SEQ ID NO: 33.

5. The peptide according to claim 1 comprising SEQ ID NO: 34.

6. The peptide according to claim 1 comprising SEQ ID NO: 35.

7. The peptide according to claim 1 comprising SEQ ID NO: 36.

8. The peptide according to claim 1 or 2 characterized in that the peptide has the capacity to inhibit the biological activity of TGF-β1 in vitro and/or in vivo.

9. A method of making a pharmaceutical composition, said method comprising introducing the peptide of claim 1 or 2 into a pharmaceutically acceptable excipient.

10. A pharmaceutical composition comprising the peptide of claim 1 or 2 and at least one pharmaceutically acceptable excipient.

* * * * *

UNITED STATES PATENT AND TRADEMARK OFFICE
CERTIFICATE OF CORRECTION

| | |
|---|---|
| PATENT NO. | : 7,666,841 B2 |
| APPLICATION NO. | : 10/569012 |
| DATED | : February 23, 2010 |
| INVENTOR(S) | : De Las Herrerías et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,666,841 B2 |
| APPLICATION NO. | : 10/569012 |
| DATED | : February 23, 2010 |
| INVENTOR(S) | : Dotor De Las Herrerias et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this

Twenty-first Day of December, 2010

David J. Kappos
*Director of the United States Patent and Trademark Office*